(12) United States Patent
Holt

(10) Patent No.: US 6,719,801 B1
(45) Date of Patent: Apr. 13, 2004

(54) APPARATUS CONFIGURATION AND METHOD FOR TREATING A FOOT

(76) Inventor: Edward S. Holt, 3 Severn Ct., Annapolis, MD (US) 21403

( * ) Notice: Subject to any disclaimer, the term of this patent is extended or adjusted under 35 U.S.C. 154(b) by 0 days.

(21) Appl. No.: 10/028,294

(22) Filed: Dec. 28, 2001

Related U.S. Application Data

(62) Division of application No. 09/599,852, filed on Jun. 23, 2000, now Pat. No. 6,576,018.

(51) Int. Cl.[7] .................................................. A61F 2/42
(52) U.S. Cl. ................ 623/21.11; 623/21.19; 623/902; 606/60
(58) Field of Search ................ 623/11.11, 16.11, 623/21.11, 21.18–21.19, 23.47, 66.1, 902, 908, 18.11, 21.12, 21.15; 606/60, 151; 128/898; 600/587, 592

(56) References Cited

U.S. PATENT DOCUMENTS

| | | | | |
|---|---|---|---|---|
| 3,745,590 A | * | 7/1973 | Stubstad | 623/13.11 |
| 4,409,974 A | * | 10/1983 | Freedland | 606/60 |
| 4,969,909 A | * | 11/1990 | Barouk | 623/21.15 |
| 5,529,075 A | * | 6/1996 | Clark | 128/898 |

* cited by examiner

*Primary Examiner*—David H. Willse
*Assistant Examiner*—Urmi Chattopadhyay
(74) *Attorney, Agent, or Firm*—Jackson Patent Law Office

(57) ABSTRACT

Disclosed are a prosthesis configuration and method for treating acquired flatfoot. In an exemplary embodiment of the invention, a member is positioned between a first bone in the foot and a second bone in the foot, such that the first and second bones are separated by a third bone, and a maximum force in the member is a tension force when the foot is under a standing load. The member is longitudinal and flexible.

31 Claims, 5 Drawing Sheets

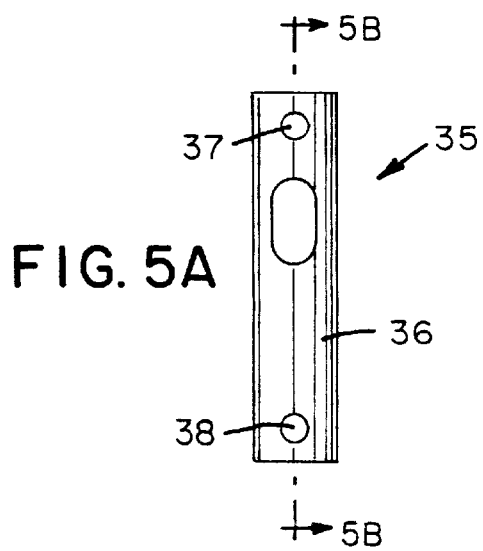
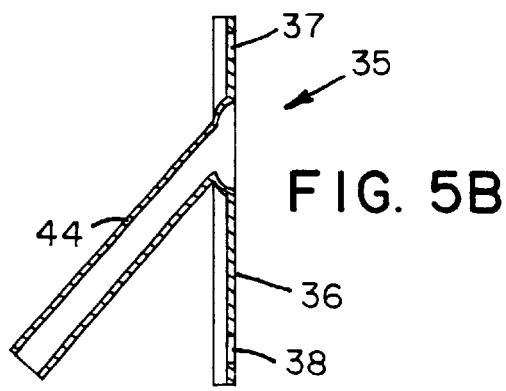
FIG. 5A
FIG. 5B
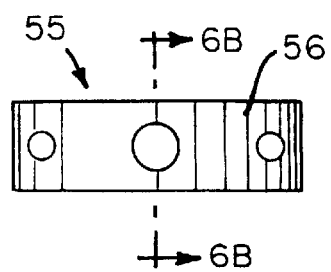
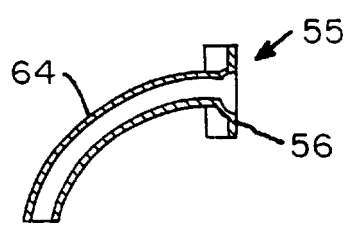
FIG. 6A
FIG. 6B
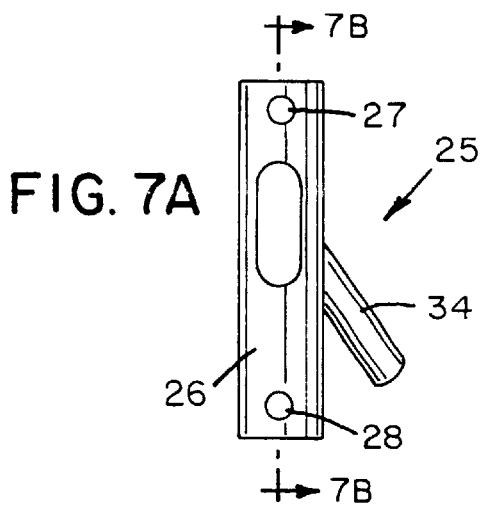
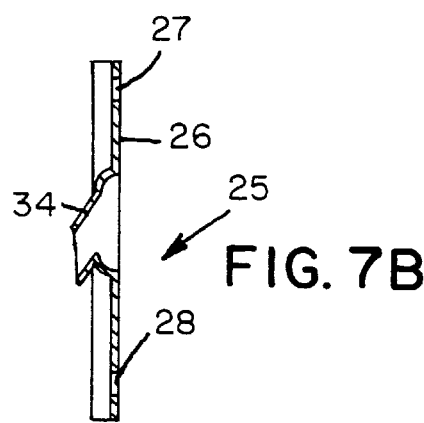
FIG. 7A
FIG. 7B

APPARATUS CONFIGURATION AND METHOD FOR TREATING A FOOT

This Application is a Divisional of U.S. application Ser. No. 09/599,852 of Edward S. HOLT filed Jun. 23, 2000 for APPARATUS CONFIGURATION AND METHOD FOR TREATING FLATFOOT, now U.S. Pat. No. 6,576,018, the contents of which are herein incorporated by reference.

BACKGROUND OF THE INVENTION

1. Field of the Invention

This invention relates generally to medical devices and, more particularly, to an apparatus and method for treating acquired flatfoot.

2. Description of Related Art

Many adults develop a painful breakdown and deformity of the arch of the foot. Procedures to correct this deformity have required cutting and realigning or fusing bones in the foot.

SUMMARY OF THE INVENTION

It is an object of the present invention to provide an apparatus configuration and method for treating acquired flatfoot, while minimizing the need to fuse bones in the foot.

To achieve this and other objects of the present invention, there is method of installing a prosthesis in a foot. The method comprises positioning a first member between a first bone in the foot, and a second bone in the foot, the first member being longitudinal and flexible, such that the first and second bones are separated by a third bone in the foot, and a maximum force in the first member is a tension force when the foot is under a standing load.

BRIEF DESCRIPTION OF THE DRAWINGS

FIGS. 5A is a view of yet another element of the first preferred apparatus.

FIG. 5B is a view taken along the line 5B—5B in FIG. 5A.

FIGS. 6A is a view of yet another element of the first preferred apparatus.

FIG. 6B is a view taken along the line of 6B—6B in FIG. 6A.

FIGS. 7A is a view of yet another element of the first preferred apparatus.

FIG. 7B is a view taken along the line 7B—7B in FIG. 7A.

The accompanying drawings which are incorporated in and which constitute a part of this specification, illustrate embodiments of the invention and, together with the description, explain the principles of the invention, and additional advantages thereof. Throughout the drawings, corresponding parts are labeled with corresponding reference numbers.

DESCRIPTION OF THE PREFERRED EMBODIMENTS

Figure 1:
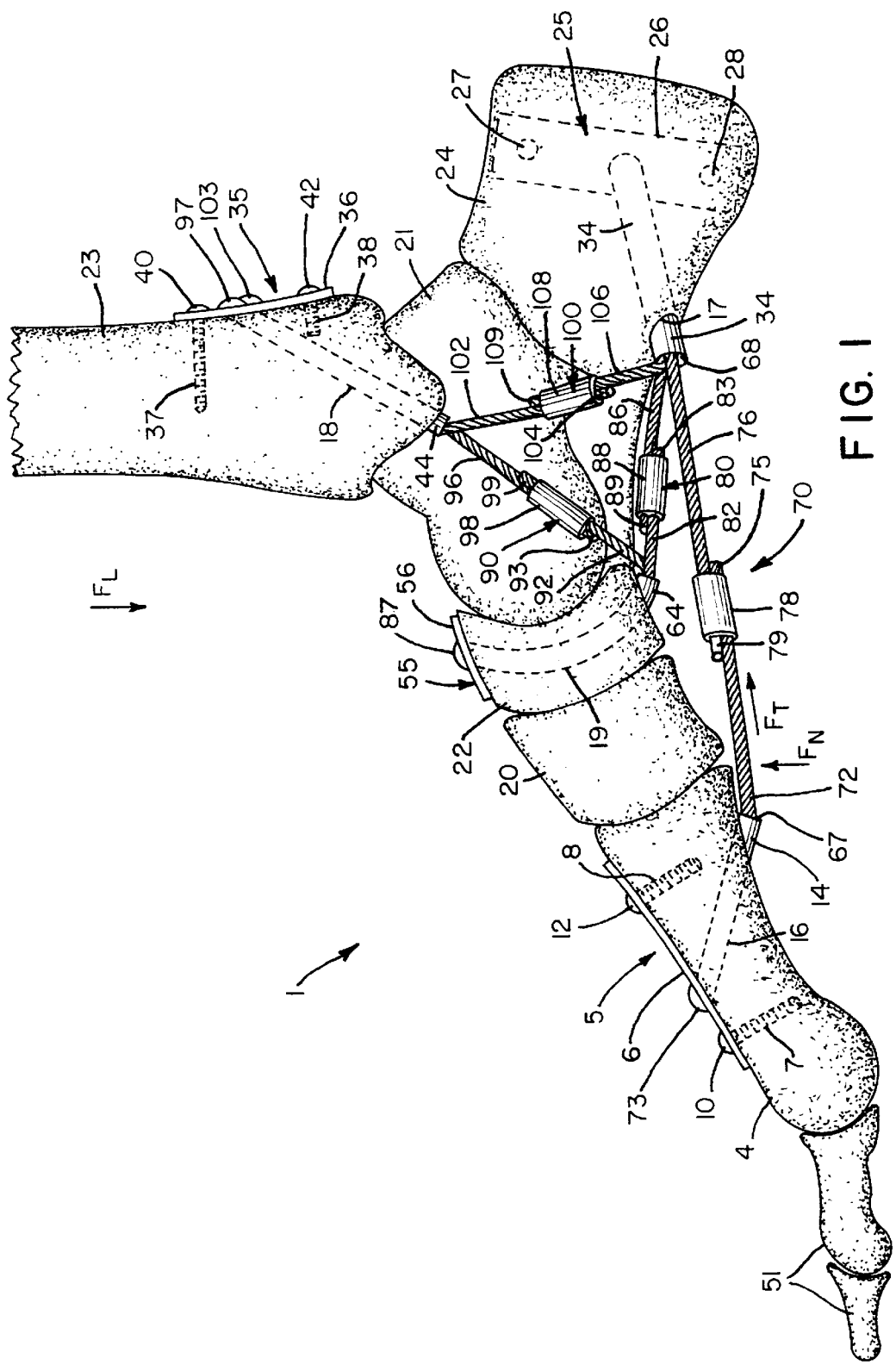
FIG. 1 is a side view of an apparatus for treating flatfoot in accordance with a first embodiment of the present invention.
Figure 2:
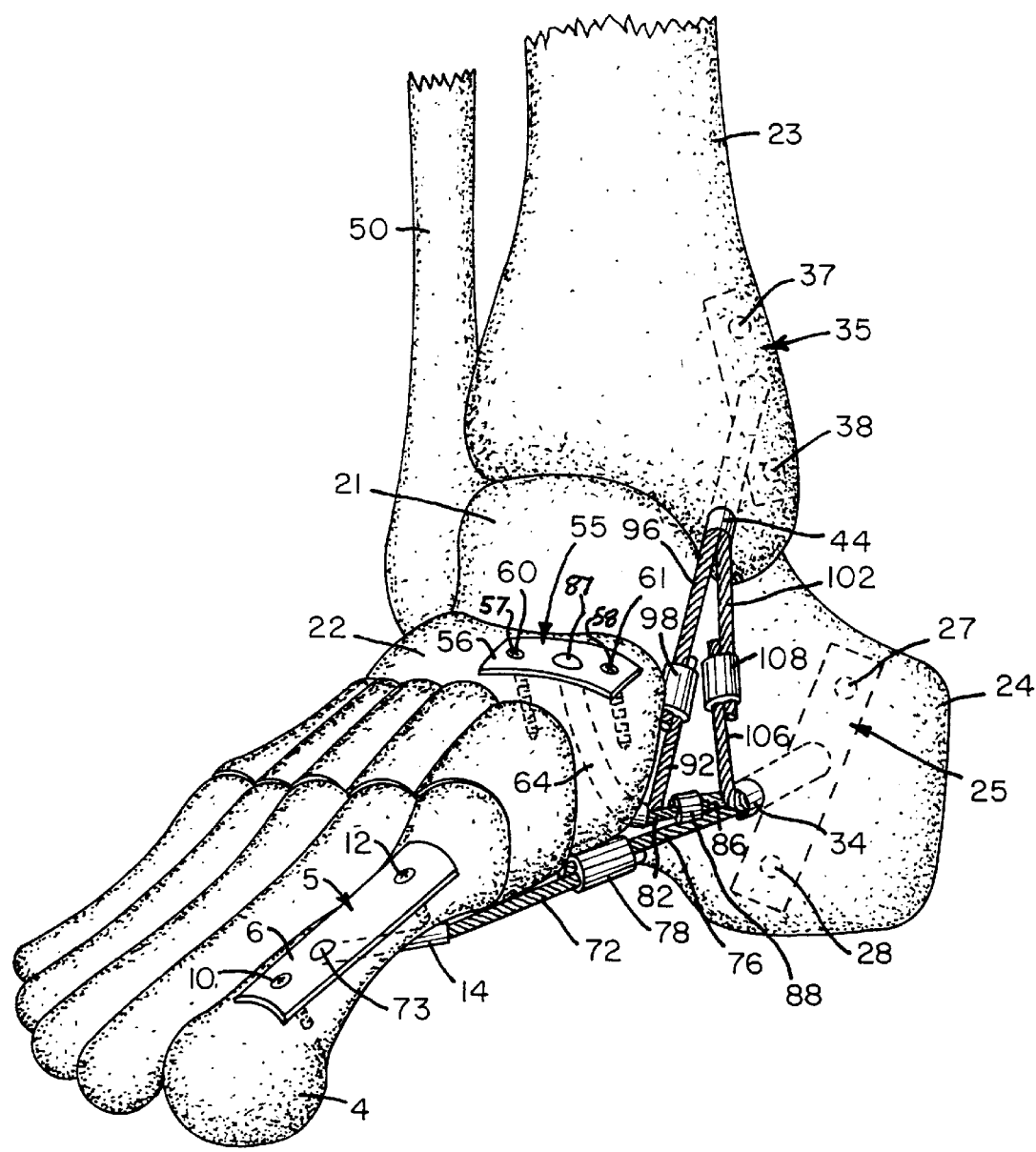
FIG. 2 is a perspective, partial view corresponding to FIG. 1.

FIGS. 1 and 2 show prosthesis configuration 1 including anchor assembly 5 on first metatarsal bone 4, anchor assembly 25 on heel bone 24, and cable assembly 70 coupled between anchor assemblies 5 and 25. Anchor assembly 5 includes backing plate 6 and tube 14 integrally connected with plate 6. Tube 14 is located in bone through-hole 16 defined in first metatarsal bone 4. Plate 6 defines a contour that fits a contour of bone 4, to distribute load transmitted from flexible, metal cable 72 over the surface of bone. In this patent application, the term "cable" means a plurality of filaments or lines attached along the longitudinal dimension by twisting or braiding.

Plate 6 defines holes 7 and 8. Bone screw 10 is screwed into bone 4 via hole 7, and bone screw 12 is screwed into bone 4 via hole 8.

FIGS. 1 and 2 also show fibula bone 50 and other bones 51.

Anchor assembly 25 includes backing plate 26 and tube 34 integrally connected with plate 26. Tube 34 is located in bone through-hole 17 defined in bone 24. Plate 26 defines a contour that fits a contour of bone 24, to distribute load transmitted from flexible, metal cable 76 over the surface of bone 24. Plate 26 defines holes 27 and 28.

Flexible, metal cable 72 is engaged with assembly 5 through tube 14. Flexible, metal cable 72 has stop 73 fixed to the end of cable 72. Stop 73 acts as a type of flange to prevent cable 72 from slipping out of tube 14.

Flexible, metal cable 72 is attached to flexible, metal cable 76 via compressible sleeve 78. Flexible, metal cable 76 is engaged with anchor assembly 25 via tube 34.

Figure 3:
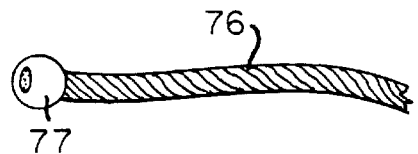
FIG. 3 is a view of an element of the first preferred apparatus.

As shown in FIG. 3, Flexible, metal cable 76 has stop 77 fixed to the end of cable 76, to prevent cable 76 from slipping out of tube 34. Cable 76 includes metallic filament 84 and metallic filament 85. The longitudinal dimension of filament 84 is attached to the longitudinal dimension filament 85, by twisting.

As shown in FIG. 1, anchor assembly 55 is on navicular bone 22, anchor assembly 35 is on tibia bone 23, and cable assembly 90 is coupled between anchor assemblies 55 and 35. Anchor assembly 55 includes backing plate 56 and curved tube 64 integrally connected with plate 56. Plate 56 defines a contour that fits a contour of bone 22, to distribute load transmitted from flexible, metal cable 92 over the surface of bone 22. Plate 56 defines holes 57 and 58. Bone screw 60 is screwed into bone 22 via hole 57, and bone screw 61 is screwed into bone 22 via hole 58.

Tube 64 is located in curved, bone through-hole 19 defined in navicular bone 22. Tube 64 has a constant radius of curvature, allowing tube 64 to be guided through through-hole 19.

Anchor assembly 35 includes backing plate 36 and curved tube 44 integrally connected with plate 36. Tube 44 is located in bone through-hole 18 defined in tibia bone 23. Plate 36 defines a contour that fits a contour of bone 23, to distribute load transmitted from flexible, metal cable 96 over the surface of bone 23. Plate 36 defines holes 37 and 38. Bone screw 40 is screwed into bone 23 via hole 37, and bone screw 42 is screwed into bone 23 via hole 38.

Flexible, metal cable 92 is engaged with assembly 55 through tube 64. Flexible, metal cables 92 and 82 share a common tube 64. Flexible, metal cable 82 has stop 87 fixed to the end of flexible, metal cable 82. Stop 87 acts as a type of flange to prevent flexible, metal cable 82 from slipping out of tube 64. Flexible, metal cable 92 has a stop (not shown in FIG. 1) fixed to the end of cable 92. The stop at the end of flexible, metal cable 92 acts as a type of flange to prevent cable 92 from slipping out of tube 64.

Flexible, metal cable 92 is attached to flexible, metal cable 96 via compressible sleeve 98.

Flexible, metal cable 96 and flexible, metal cable 102 share a common tube 44. Flexible, metal cable 96 is engaged with anchor assembly 35 via tube 44. Flexible, metal cable 96 has stop 97 fixed to the end of cable 96. Stop 97 acts as a type of flange to prevent flexible, metal cable 96 from slipping out of tube 44. Flexible, metal cable 102 has stop 103 fixed to the end of cable 102. Stop 103 acts as a type of flange to prevent flexible, metal cable 102 from slipping out of tube 44.

Each cable assembly in the prosthesis is inside of the body, under the skin.

Referring to FIG. 1, the foot is under a load $F_L$ of 50 pounds or more as when, for example, the person is standing up. $F_L$, which is a type of standing load, is delivered to the foot via tibia 23 and fibula 50. Cable assembly 70 extends into metatarsal 4 and heel 24. Cable assembly 70 defines a length between position 67 on assembly 70 and position 68 on assembly 70. Cable assembly 70 is positioned and oriented such that a maximum force, on most of this length, is a tension force, meaning that the force is directed along the length of cable assembly 70. Although pressure from body tissue or bone may cause a force $F_N$ perpendicular to cable assembly 70, on most of the length, $F_T$ is greater then $F_N$.

With the load $F_L$, each cable assembly has a tension force that is the maximum force on most of the length of the cable assembly between the two anchor bones of the assembly, as described above in connection with assembly 70.

Prosthesis configuration 1 is assembled to restore the arch and prevent its future collapse. More specifically, to assemble prosthesis 1, first make bone through-holes 16, 19, 17, and 18 in metatarsal bone 4, navicular bone 22, heel bone 24, and tibia bone 23, respectively. Next, attach assembly 5 to bone 4 by placing tube 14 in through-hole 16, screwing screw 10 into bone 4 via hole 7, and screwing screw 12 into bone 4 via hole 8. Attach assembly 25 to bone 24 by placing tube 34 in through-hole 17, screwing a screw (not shown) into bone 24 via hole 27, and screwing a screw (not shown) into bone 24 via hole 28. Attach assembly 55 to bone 22 by placing tube 64 in through-hole 19, screwing screw 60 into bone 22 via hole 57, and screwing screw 61 into bone 22 via hole 58. Attach assembly 35 to bone 23 by placing tube 44 in through-hole 18, screwing screw 40 into bone 23 via hole 37, and screwing screw 42 into bone 23 via hole 38.

Next, pass distal end 75 of flexible, metal cable 72 through tube 14 and pass distal end 79 of flexible, metal cable 76 through tube 34. Align distal end 75 with distal end 79 and surround distal ends 75 and 79 with compressible sleeve 78. Compress compressible sleeve 78 to fix the movement of distal end 75 relative to distal end 79, thereby setting the length of cable assembly 70. In setting the length of cable assembly 70, tension cable assembly 70 appropriately to correct the deformity, by pulling the forefoot and heel into a slightly over arched position, such that, when the foot bears load, the proper longitudinal arch is established.

Thus, cable assembly 70 extends from heel bone 24 to metatarsal bone 4, under cuboid bone 20, navicular bone 22 and talus bone 21.

In other words, assembly 70 extends into bone 4 and extends into bone 24. Bones 4 and 24 are separated by bone 20. Bones 4 and 24 are also separated by bone 22. Bones 4 and 24 are also separated by bone 21. Assembly 70 is positioned and oriented such that, in loaded tension, a maximum force is a tension force when the foot is under a standing load.

Pass distal end 99 of flexible, metal cable 92 through tube 64 and pass distal end 93 of flexible, metal cable 96 through tube 44. Align distal end 99 with distal end 93 and surround distal ends 99 and 93 with compressible sleeve 98. Compress compressible sleeve 98 to fix the movement of distal end 99 relative to distal end 93, thereby setting the length of cable assembly 90. In setting the length of cable assembly 90, tension cable assembly 90 to correct forefoot abduction. Thus, cable assembly 90 extends from tibia bone 23 to navicular bone 22 on the inboard side of talus bone 21.

Pass distal end 104 of flexible, metal cable 102 through tube 44 and pass distal end 109 of flexible, metal cable 106 through tube 34. Align distal end 104 with distal end 109 and surround distal ends 104 and 109 with compressible sleeve 108. Compress compressible sleeve 108 to fix the movement of distal end 104 relative to distal end 109, thereby setting the length of cable assembly 100. In setting the length of cable assembly 100, tension cable assembly 100 to correct hind foot valgus, to restore heel 24 to neutral alignment. Thus, cable assembly 100 extends from tibia bone 23 to heel bone 24 on the inboard side of talus bone 21.

Pass distal end 83 of flexible, metal cable 82 through tube 64 and pass distal end 89 of flexible, metal cable 86 through tube 34. Align distal end 83 with distal end 89 and surround distal ends 83 and 89 with compressible sleeve 88. Compress compressible sleeve 88 to fix the movement of distal end 83 relative to distal end 89, thereby setting the length of cable assembly 80. In setting the length of cable assembly 80, tension cable assembly 80 to correct forefoot valgus, restoring neutral alignment of the forefoot. Thus, cable assembly 80 extends from navicular bone 22 to heel bone 24 under talus bone 21.

Thus, flexible, metal cables 76, 86, and 106 share tube 34.

Figure 4A:
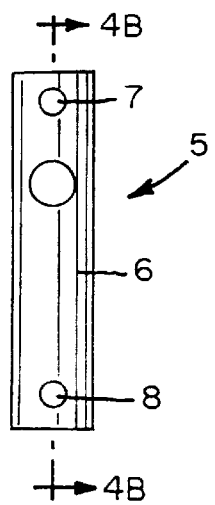
FIG. 4A is a view of another element of the first preferred apparatus.
Figure 4B:
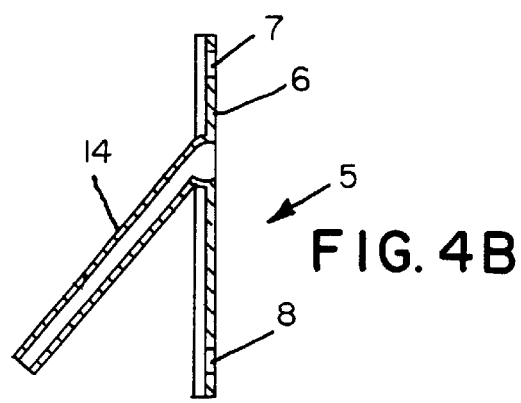
FIG. 4B is a view taken along the line 4B—4B in FIG. 4A.

FIG. 4A shows a front view of anchor assembly 5, and FIG. 4B shows a cross-sectional view corresponding to the line 4B—4B in FIG. 4A.

FIG. 5A shows a front view of anchor assembly 35, and FIG. 5B shows a cross-sectional view corresponding to the line 5B—5B in FIG. 5A.

FIG. 6A is a front view anchor assembly 55, and FIG. 6B shows a cross-sectional view corresponding to the line 6B—6B in FIG. 6A.

FIG. 7A shows a front view of anchor assembly 25, and FIG. 7B shows a cross-sectional view corresponding to the line 7B—7B in FIG. 7A.

Each of flexible, metal cables 72, 76, 92, 96, 82, 86, 102, and 106 is 7×19 stainless cable. These cables may also be another flexible material, such as braided SPECTRA or KEVLAR.

In summary, the preferred prosthesis includes flexible cables with end stops already swaged (permanently affixed) in place, anchor assemblies of appropriate shape and fitted with a rigidly fixed (e.g. welded) tube shaped variously for different bones, and compressible metal sleeves. Appropriate bones are drilled to accommodate the tubular portion of the backing plate. The assembly plates are applied to these bones. A flexible cable with end stop has then been passed through each plate and the appropriate cables are connected together with a compressible sleeve under appropriate tension.

With the cables pulled in appropriate tension, a more appropriate anatomic relationship of the foot is established. The patient may be able to bear weight soon after surgery since the device does not depend on healing for its stability.

The backing plates may also include a porous coating on the undersurface of the plate to allow bone ingrowth to the plate.

Figure 8:
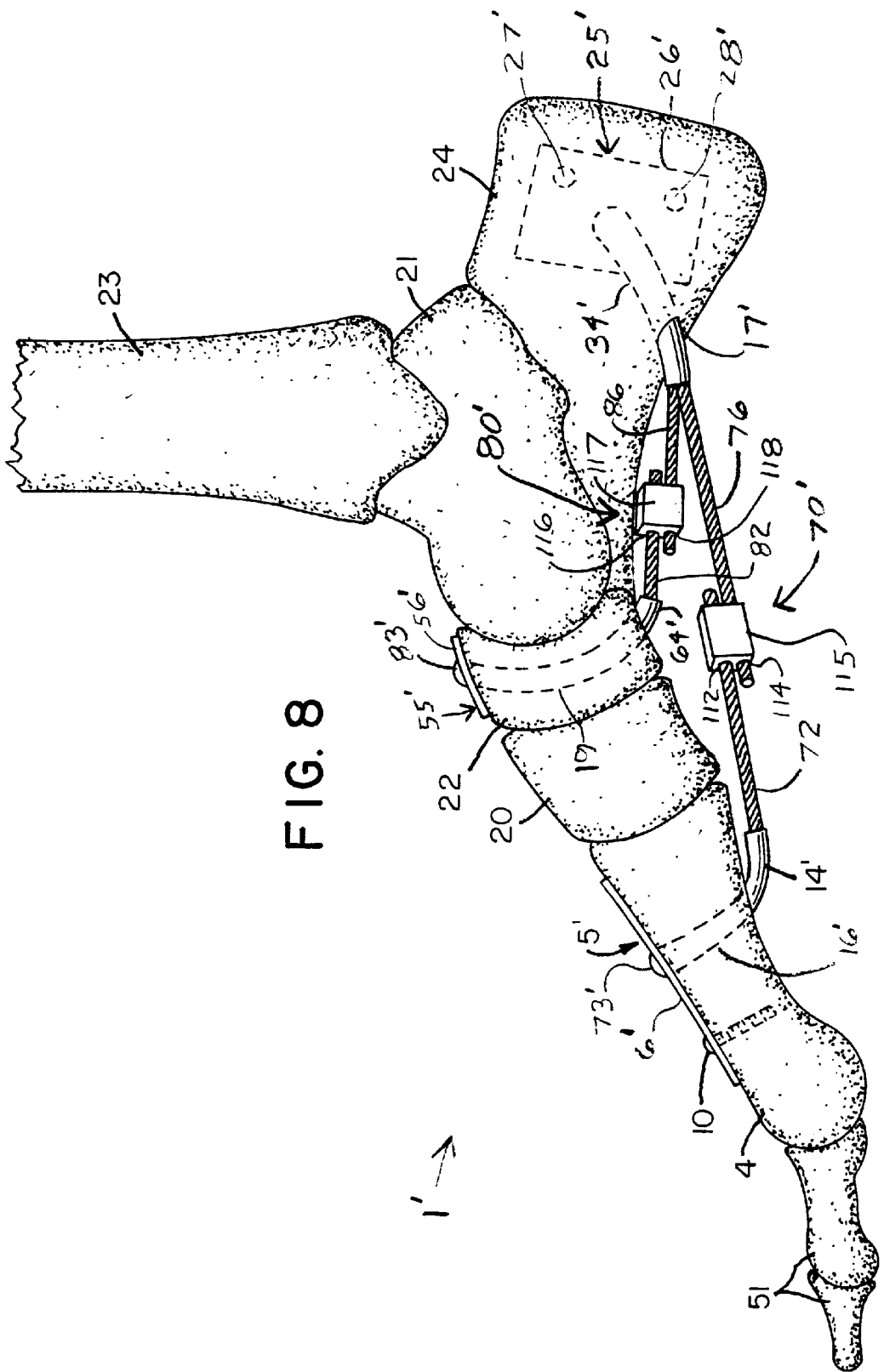
FIG. 8 is a side view of an apparatus for treating flatfoot in accordance with a second embodiment of the present invention.

FIG. 8 shows prosthesis configuration 1' in accordance with a second embodiment of the present invention. Prosthesis configuration 1' including anchor assembly 5' on first metatarsal bone 4, anchor assembly 25' on heel bone 24, and cable assembly 70' coupled between anchor assemblies 5' and 25'. Anchor assembly 5' includes backing plate 6' and tube 14' integrally connected with plate 6'. Tube 14' is located in bone through-hole 16' defined in first metatarsal bone 4. Plate 6 defines a contour that fits a contour of bone 4, to distribute load transmitted from flexible, metal cable 72 over the surface of bone 4.

Anchor assembly 25' includes backing plate 26' and tube 34' integrally connected with plate 26'. Tube 34' is located in bone through-hole 17' defined in bone 24. Plate 26' defines a contour that fits a contour of bone 24, to distribute load transmitted from flexible, metal cable 76 over the surface of bone 24. Plate 26' defines holes 27' and 28'.

Flexible, metal cable 72 is engaged with assembly 5' through tube 14'. Flexible, metal cable 72 has stop 73' fixed to the end of cable 72. Stop 73' acts as a type of flange to prevent cable 72 from slipping out of tube 14'.

Flexible, metal cable 72 is attached to flexible, metal cable 76 via block 115. More specifically, block 115 defines holes 112 and 114. Cable 72 is passed through hole 112 and engaged with hole 112 via a mechanism such as a screw, for example. Cable 76 is engaged with hole 114 to adjust the tension of cable assembly 70'.

Flexible, metal cable 76 is engaged with anchor assembly 25' via tube 34'.

Anchor assembly 55' is on navicular bone 22. Anchor assembly 55' includes backing plate 56' and curved tube 64' integrally connected with plate 56'.

Flexible, metal cable 82 is engaged with assembly 55' through tube 64'. Flexible, metal cable 82 has stop 83' fixed to the end of cable 82. Stop 83' acts as a type of flange to prevent cable 82 from slipping out of tube 64'.

Flexible, metal cable 82 is attached to flexible, metal cable 86 via block 117. Block 117 defines holes 116 and 118. Cable 82 is passed through hole 116 and engaged with hole 116 via a mechanism such as a screw, for example. Cable 86 is engaged with hole 118 to adjust the tension of cable assembly 80'.

Flexible, metal cable 86 is engaged with anchor assembly 25' via tube 34'.

Additional advantages and modifications will readily occur to those skilled in the art. The invention in its broader aspects is therefore not limited to the specific details, representative apparatus, and illustrative examples shown and described. Accordingly, departures may be made from such details without departing from the spirit or the scope of Applicants' general inventive concept. The invention is defined in the following claims.

What is claimed is:

1. A method of installing a prosthesis in a foot, the method comprising:

positioning a first member between a first bone in the foot, and a second bone in the foot, the first member being longitudinal and flexible, such that the first and second bones are separated by a third bone in the foot and a maximum force in the first member is a tension force when the foot is under a standing load, wherein positioning includes engaging a first part with the first bone;

engaging a second part with the second bone; and subsequently attaching the first dart to the second part, to assemble the first member, wherein attaching includes securing a sleeve around the first and second parts.

2. The method of claim 1 wherein positioning includes making a first through-hole in the first bone, and a second through-hole in the second bone.

3. The method of claim 2 wherein positioning further includes positioning the first member such that the first member is in the first and second through-holes.

4. The method of claim 3 further including placing a first channel member in the first through-hole and a second channel member in the second through-hole.

5. The method of claim 4 wherein the first channel member defines a cross-section having an arc shape.

6. The method of claim 4 wherein the first channel member includes a tube.

7. The method of claim 1 wherein attaching acts to selectively set a length of the first member, to pull the forefoot and heel into a position, such that, when the foot bears load, a proper longitudinal arch is established.

8. The method of claim 7 further including engaging a first plate with the first bone, wherein engaging the first part includes engaging the first part with the first plate.

9. The method of claim 8 wherein engaging the first part with the first plate includes engaging via a flange.

10. The method of claim 8 wherein engaging the first plate with the first bone includes placing the first plate on the first bone; and extending a fastener through the first plate and first bone.

11. The method of claim 1 wherein the first bone is a metatarsal bone and the second bone is a heel bone.

12. The method of claim 1 further including positioning a second member between the second bone, and a fourth bone in the foot, the second member being longitudinal and flexible.

13. The method of claim 12 wherein positioning the second member includes making a through-hole in the second bone.

14. The method of claim 13 wherein positioning the second member further includes positioning the second member such that the second member is in the through-hole, and wherein positioning the first member includes positioning the first member such that the first member is in the through-hole.

15. The method of claim 14 further including placing a channel member in the through-hole.

16. The method of claim 14 further including placing a tube in the through-hole.

17. The method of claim 1 further including positioning a second member between a fourth bone in the foot, and a fifth bone in the foot, the second member being longitudinal and flexible.

18. The method of claim 17 wherein positioning the second member includes
   making a first through-hole in the fourth bone, and a second through-hole in the fifth bone.

19. The method of claim 18 wherein positioning the second member further includes positioning the second member such that the second member is in the first and second through-holes.

20. The method of claim 19 further including placing a first channel member in the first through-hole and a second channel member in the second through-hole.

21. The method of claim 19 further including placing a first channel member in the first through-hole and a second channel member in the second through-hole, wherein the first channel member defines a cross section having an arc shape.

22. The method of claim 20 further including placing a first tube in the first through-hole and a tube in the second through-hole.

23. The method of claim 17 further including
   engaging a first part with the fourth bone;
   engaging a second part with the fifth bone; and
   subsequently attaching the first part to the second part, to assemble the second member.

24. The method of claim 23 wherein attaching includes securing a sleeve around the first and second parts.

25. The method of claim 23 wherein attaching acts to selectively set a length of the second member.

26. The method of claim 23 further including
   engaging a first plate with the fourth bone, wherein engaging the first part includes engaging the first part with the first plate.

27. The method of claim 17 wherein the fourth bone is a navicular bone and the fifth bone is a tibia bone.

28. A method of installing a prosthesis in a foot, the method comprising:
   positioning a first member between a first bone in the foot, and a second bone in the foot, the first member being longitudinal and flexible, such that the first and second bones are separated by a third bone in the foot, and a maximum force in the first member is a tension force when the foot is under a standing load, wherein positioning includes
   engaging a first part with the first bone;
   engaging a second part with the second bone; and
   subsequently attaching the first part to the second part, to assemble the first member, to selectively set a length of the first member, to pull the forefoot and heel into a position, such that, when the foot bears load, a proper longitudinal arch is established.

29. A method of installing a prosthesis in a foot, the method comprising:
   positioning a first member between a first bone in the foot, and a second bone in the foot, the first member being longitudinal and flexible, such that the first and second bones are separated by a third bone in the foot, and a maximum force in the first member is a tension force when the foot is under a standing load, wherein the first bone is a metatarsal bone and the second bone is a heel bone.

30. A method of installing a prosthesis in a foot, the method comprising:
   positioning a first member between a first bone in the foot, and a second bone in the foot, the first member being longitudinal and flexible, such that the first and second bones are separated by a third bone in the foot, and a maximum force in the first member is a tension force when the foot is under a standing load; and
   positioning a second member between the second bone, and a fourth bone in the foot, the second member being longitudinal and flexible.

31. A method of installing a prosthesis in a foot, the method comprising:
   positioning a first member between a first bone in the foot, and a second bone in the foot, the first member being longitudinal and flexible, such that the first and second bones are separated by a third bone in the foot, and a maximum force in the first member is a tension force when the foot is under a standing load; and
   positioning a second member between a fourth bone in the foot, and a fifth bone in the foot, the second member being longitudinal and flexible.

* * * * *